US008350080B2

(12) United States Patent
Klug et al.

(10) Patent No.: US 8,350,080 B2
(45) Date of Patent: Jan. 8, 2013

(54) METHOD FOR THE PRODUCTION OF ACYL GLYCINATES BY MEANS OF DIRECT OXIDATION

(75) Inventors: Peter Klug, Grossostheim (DE); Achim Stankowiak, Altoetting (DE); Oliver Franke, Munich (DE); Franz-Xaver Scherl, Burgkirchen (DE); Ulf Pruesse, Braunschweig (DE); Nadine Decker, Erkner (DE); Klaus-Dieter Vorlop, Braunschweig (DE)

(73) Assignee: Clariant Finance (BVI) Limited, Tortola (BV)

( * ) Notice: Subject to any disclaimer, the term of this patent is extended or adjusted under 35 U.S.C. 154(b) by 341 days.

(21) Appl. No.: 12/812,011

(22) PCT Filed: Jan. 7, 2009

(86) PCT No.: PCT/EP2009/000034
§ 371 (c)(1),
(2), (4) Date: Aug. 12, 2010

(87) PCT Pub. No.: WO2009/087086
PCT Pub. Date: Jul. 16, 2009

(65) Prior Publication Data
US 2010/0305358 A1   Dec. 2, 2010

(30) Foreign Application Priority Data
Jan. 10, 2008  (DE) .................. 10 2008 003 825

(51) Int. Cl.
*C07C 231/12* (2006.01)
(52) U.S. Cl. ........... 562/526; 562/538; 562/539; 554/63
(58) Field of Classification Search .............. None
See application file for complete search history.

(56) References Cited

U.S. PATENT DOCUMENTS

| 6,703,517 | B2 | 3/2004 | Hattori et al. |
| 6,828,452 | B2 | 12/2004 | Raths et al. |
| 2005/0085651 | A1 | 4/2005 | Kitamura et al. |
| 2010/0273879 | A1 | 10/2010 | Klug et al. |
| 2010/0286418 | A1 | 11/2010 | Klug et al. |

FOREIGN PATENT DOCUMENTS

| EP | 1314717 | 5/2003 |
| EP | 1672055 | 6/2006 |
| JP | 8053693 | 2/1996 |
| JP | 11 246473 | 9/1999 |
| WO | WO96/39375 | 12/1996 |
| WO | WO02/057217 | 7/2002 |
| WO | WO2008000648 | 1/2008 |
| WO | WO2008000671 | 1/2008 |
| WO | WO 2008019807 | 2/2008 |

OTHER PUBLICATIONS

International Search Report for PCT/EP2007/007128, 2007.
Translation of International Preliminary Examination Report for PCT/EP2007/007128, 2007.
L. Prati. G. Martra, Gold Bull. 39 (1999) 96.
L. Prati, F. Porta, Applied catalysis A: General 291 (2005) 199-203.
S. Biella, G.L. Castiglioni, C. Fumagalli, L Prati, M. Rossi, Catalysis Today 72 (2002) 43-49.
International Search Report for PCT/EP2008/009646, 2008.
Translation of International Preliminary Examination Report for PCT/EP2008/009646, 2008.
International Search Report for PCT/EP2009/000034, 2009.
Translation of International Preliminary Examination Report for PCT/EP2009/000034, 2009.
English Abstract for JP 11 246473, 1999.
English Abstract for JP 8053693, 1996.
Choji Kashima et al: "Amino alcohols as C- terminal protecting groups in peptide synthesis" J. Chem Soc. Perkin Trans I, vol. 3 1988, pp. 535-539.

*Primary Examiner* — Yevegeny Valenrod
(74) *Attorney, Agent, or Firm* — Tod A. Waldrop

(57) ABSTRACT

A method is described for producing acyl glycinate salts of formula (II)

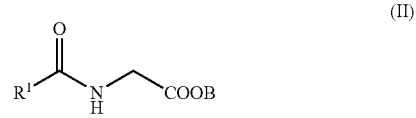

in which $R^1$ represents a saturated linear or branched alkyl radical comprising 1 to 21 carbon atoms or a monounsaturated or polyunsaturated linear or branched alkenyl radical comprising 2 to 21 carbon atoms, and B represents a cation, and/or the corresponding protonated acyl glycinic acid. Said method is characterized in that one or more fatty acid monoethanol amides of formula (I)

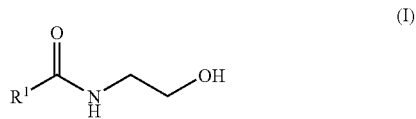

in which $R^1$ has the meaning indicated above is/are oxidized with oxygen in the presence of an optionally supported bimetallic catalyst consisting of gold and a metal from group VIII of the periodic table in the alkaline medium in order to obtain one or more acyl glycinate salts of formula (II). In order to produce the protonated acyl glycinic acids, the acyl glycinate salt/s of formula (II) is/are additionally reacted with an acid.

14 Claims, No Drawings

METHOD FOR THE PRODUCTION OF ACYL GLYCINATES BY MEANS OF DIRECT OXIDATION

Amino acid surfactants are widespread in the laundry detergents industry and cosmetics industry. They belong to the group of mild cosurfactants and are usually used for improving the foam volume and the mildness of the formulations. They have in the past been synthesized mainly by reaction of amino acids with activated fatty acid derivatives, especially fatty acid chlorides, e.g. as described in U.S. Pat. No. 6,703,517 or US 2005/0085651 A1 for acylglycinates of the formula (IIa) (see scheme 1).

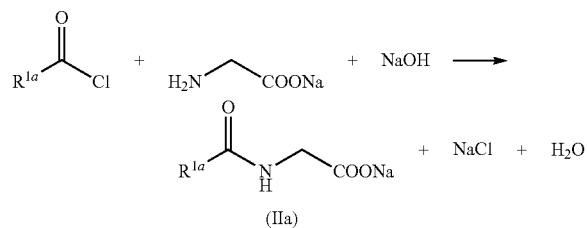

$R^{1a}$ is a saturated or unsaturated fatty acid radical having from 8 to 22 carbon atoms
Scheme 1 Preparation of Sodium Acylglycinates According to the Prior Art.

This process according to the prior art requires a relatively expensive and reactive raw material, namely the fatty acid chloride, and has the further disadvantage that one mole of sodium chloride NaCl is formed per mole of amino acid surfactant, i.e. the compound of the formula (IIa). This sodium chloride goes into the wastewater from the reaction and there represents a problem for biological water treatment plants since sodium chloride can impair the purification performance of such plants.

There is thus a need for a process for preparing amino acid surfactants, especially amino acid surfactants based on the amino acid glycine, known as acylglycinates and their protonated parent acids, which do not have the abovementioned disadvantages.

It has surprisingly been found that acylated glycines and salts thereof, known as acylglycinate salts or acylglycinates for short, can also be obtained, as an alternative to the customary fatty acid chloride route according to the prior art, by direct oxidation of fatty acid monoethanolamides by means of atmospheric oxygen or pure oxygen in the presence of transition metal catalysts.

The present invention accordingly provides a process for preparing acylglycinate salts of the formula (II)

where
$R^1$ is a saturated linear or branched alkyl radical having from 1 to 21 carbon atoms or a monounsaturated or polyunsaturated linear or branched alkenyl radical having from 2 to 21 carbon atoms and B is a cation,
and/or the corresponding protonated acylglycine acids, which comprises oxidizing one or more fatty acid monoethanolamides of the formula (I)

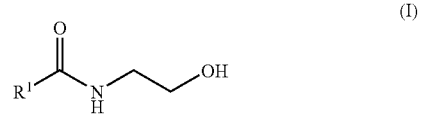

where $R^1$ is as defined above,
by means of oxygen in the presence of an optionally supported bimetal catalyst consisting of gold and a metal from group VIII of the Periodic Table of Elements in alkaline medium to form one or more acylglycinate salts of the formula (II) and, in the case of the preparation of the protonated acylglycine acids, additionally reacting the acylglycinate salt or salts of the formula (II) with an acid.

In the context of the present invention, metals from Group VIII of the Periodic Table of Elements are understood to include the metals Fe, Ru, Os, Co, Rh, Ir, Ni, Pd and Pt.

Compared to the use of the fatty acid chloride, the process of the invention starts out from a significantly cheaper raw material, viz. the fatty acid monoethanolamide of the formula (I). In addition, no salt is formed in the preparation of the acylglycinates of the formula (II) (see scheme 2).

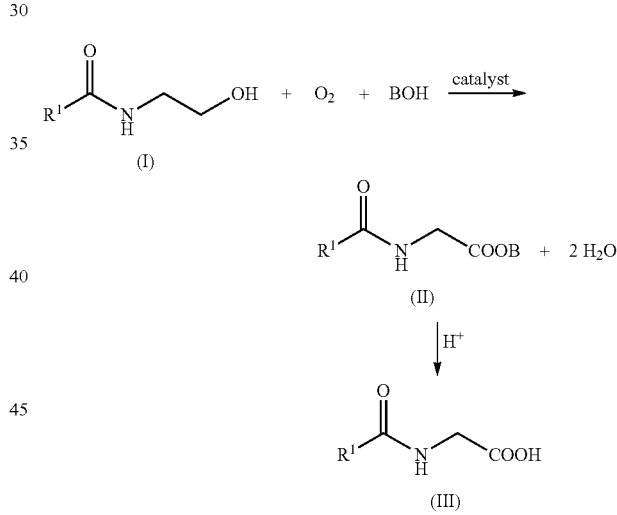

$R^1$ and B are as defined above
Scheme 2 Preparation of Acylglycinates and/or the Corresponding Protonated Acylglycine Acids by the Process of the Invention.

As fatty acid monoethanolamides, it is possible to use monoethanolamides of saturated, unbranched or branched fatty acids having 2-22 carbon atoms (i.e. $R^1=C_1-C_{21}$) or of monounsaturated or polyunsaturated, unbranched or branched fatty acids having 3-22 carbon atoms (i.e. $R^1=C_2-C_{21}$).

Preference is given to fatty acid monoethanolamides having 8-18 carbon atoms in the fatty acid radical or acyl radical $R^1CO$—, i.e. $R^1$ is in this case a saturated linear or branched alkyl radical having from 7 to 17 carbon atoms or a monounsaturated or polyunsaturated linear or branched alkenyl radical having from 7 to 17 carbon atoms. Particular preference is given to lauric acid monoethanolamide, myristic acid monoethanolamide, caprylic acid monoethanolamide, capric acid monoethanolamide, palmitic acid monoethanolamide, stearic acid monoethanolamide or isostearic acid monoethanolamide. Here, it is also possible to use amides based on chain fractions or mixtures of these fatty acid monoethanolamides, preferably coconut fatty acid monoethanolamide.

Among the saturated or unsaturated fatty acid monoethanolamides, preference is given to the saturated fatty acid monoethanolamides.

The cation B is preferably an alkali metal cation selected from among cations of the alkali metals Li, Na, K, Rb and Cs. Particular preference is given to the cations of the alkali metals Na and K.

The bimetal catalysts are mixed catalysts comprising gold together with a metal from group VIII. The bimetal catalysts are accordingly preferably gold catalysts which have been additionally doped with a metal from group VIII. They are particularly preferably doped with platinum or palladium.

The metals of the bimetal catalysts or the bimetal catalysts are preferably applied to a support. Preferred supports are activated carbon and oxidic supports, preferably oxidic supports. Preferred oxidic supports are, in turn, titanium dioxide, cerium dioxide or aluminum oxide, most preferably, the oxidic supports comprise titanium dioxide. Such catalysts can be produced by known methods such as incipient wetness (IW) or deposition precipitation (DP) as described, for example, in L. Prati, G. Martra, Gold Bull. 39 (1999) 96 and S. Biella, G. L. Castiglioni, C. Fumagalli, L. Prati, M. Rossi, Catalysis Today 72 (2002) 43-49 or L. Prati, F. Porta, Applied catalysis A: General 291 (2005) 199-203.

In a further preferred embodiment of the invention, the supported bimetal catalysts contain from 0.1 to 5% by weight and preferably from 0.5 to 3% by weight of gold.

Furthermore, the supported bimetal catalysts preferably contain from 0.1 to 3% by weight and preferably from 0.1 to 2% by weight of a metal of group VIII, preferably platinum or palladium.

The supported bimetal catalysts particularly preferably contain from 0.1 to 5% by weight, in particular from 0.5 to 3% by weight, of gold and from 0.1 to 3% by weight, in particular from 0.1 to 2% by weight, of a group VIII metal, preferably platinum or palladium, based on the sum of support material and bimetal catalyst. The preferred weight ratio of gold/group VIII metal, in particular gold/platinum or gold/palladium, is from 70:30 to 95:5. The same ratios also apply when using gold and metals of group VIII other than platinum or palladium.

The particle size of the bimetal catalyst is preferably from 1 to 50 nm and particularly preferably from 2 to 10 nm. For the purposes of the present invention, these bimetal catalysts are also referred to as nanogold catalysts.

As bases, it is possible to use carbonates, hydroxides or oxides in the process of the invention. Preference is given to the hydroxides BOH.

The process of the invention is preferably carried out in water.

The oxidation reaction is preferably carried out at a temperature of from 30 to 200° C., particularly preferably in the range from 80 to 150° C.

The pH in the oxidation is preferably in the range from 8 to 13, particularly preferably in the range from 9 to 12.

The pressure in the oxidation reaction is preferably increased above atmospheric pressure.

The reaction in the alkaline medium firstly forms the alkali metal salts (B=Li, Na, K, Rb, Cs) of the acylated glycines having from 2 to 22 carbon atoms in the acyl radical, preferably 8 to 18 carbon atoms, preferably the sodium or potassium salts. The process is particularly preferably used for sodium cocoylglycinate and potassium cocoylglycinate. The acylated glycine can then be obtained from the solutions by acidification with inorganic acids. Preferred acids are hydrochloric acid and sulfuric acid.

In a further embodiment of the invention, account is taken of the fact that relatively long-chain ($\geq C_8$) fatty acid monoethanolamides, i.e. fatty acid monoethanolamides having 8 or more carbon atoms in the acyl radical $R^1CO$—, especially lauric acid monoethanolamide and coconut fatty acid monoethanolamide, are not sufficiently soluble in the reaction medium water for a satisfactory oxidation reaction without addition of suitable solvents. The advantage of the NaCl-free production of the target substances would in this case be partly lost again due to the additional use of solvents.

It has now been found that fatty acid monoethanolamides having 8 or more carbon atoms in the acyl radical $R^1CO$—, especially lauric acid monoethanolamide and coconut fatty acid monoethanolamide, are soluble in solutions of alkali metal salts of the acylglycinates or fatty acid glycinates, in particular the alkali metal salts of lauric acid glycinates or coconut fatty acid glycinates. This results in an elegant, solvent-free process comprising preparing a solution of fatty acid monoethanolamide in the target product acylglycinate salt, preferably sodium acylglycinate (this can be carried out by backmixing of the finished reaction solution with fatty acid monoethanolamide) and subjecting this mixture to the catalytic oxidation. The monoethanolamide present is thus oxidized and a solution of an alkali metal salt (B=Li, Na, K, Rb, Cs) of the acylglycine acid of the formula (III) in water is produced. Particular preference is given here to the sodium and potassium salts (B=Na, K).

The acylglycine acid of the formula (III) can subsequently be liberated from the alkaline reaction solution by means of suitable acids. Preferred acids are hydrochloric acid and sulfuric acid.

In a preferred embodiment of the invention, a solution comprising one or more fatty acid monoethanolamides of the formula (I) and one or more acylglycinates of the formula (II) is therefore subjected to oxidation.

In this preferred embodiment of the invention, the fatty acid monoethanolamides are oxidized by means of oxygen and an optionally supported bimetal catalyst comprising gold and a metal from group VIII, in alkali medium to form solutions of acylglycinates, with a solution of the fatty acid monoethanolamide in an alkali metal salt of an acylglycinate being present before commencement of the oxidation reaction and this mixture being subjected to the oxidation reaction in water.

In this preferred embodiment of the invention, the mass ratio of fatty acid monoethanolamide of the formula (I) to acylglycinate of the formula (II) at the beginning of the reaction is in the range from 1:10 to 3:1, preferably in the range from 1:2 to 2:1. The total proportion by mass of fatty acid monoethanolamide of the formula (I) and acylglycinate of the formula (II) is in the range from 15 to 50%, preferably in the range from 20 to 40%, particularly preferably in the range from 25 to 35%.

The process of the invention preferably gives solutions of acylglycinates of the formula (II) having only small residual contents of fatty acid monoethanolamide of <10% by weight, preferably <5% by weight, particularly preferably <2% by weight.

The following examples illustrate the invention:

EXAMPLE 1

Process for Preparing Glycinates Using Gold Catalysts 1 liter of an aqueous solution containing 15% by weight of coconut fatty acid monoethanolamide and 15% by weight of sodium cocoylglycinate is placed in a 2 liter pressure autoclave provided with sparging stirrer. This mixture is clear and liquid to 80° C. The amount of sodium cocoylglycinate can be taken from a previous batch or remain in the reactor from a previous oxidation batch. After addition of 5 g of a nanogold catalyst (0.9% by weight of gold and 0.1% by weight of platinum on titanium dioxide, particle size: 4-8 nm), the suspension is brought to a pH of 12 by means of sodium hydroxide and heated to 80° C. After the reaction temperature has been reached, the reaction solution is pressurized with oxygen to a pressure of 9 bar and maintained at this pressure by introduction of further amounts. The pH of the mixture is maintained at 12 over the entire reaction time by means of sodium hydroxide introduced by means of an automatic titrator. After 6 hours, the reactor is cooled, vented and the catalyst is separated off from the reactor solution by filtration. The solution has a residual content of <2% by weight of coconut monoethanolamide and about 32% by weight of sodium cocoylglycinate.

EXAMPLE 2

Process for Preparing Glycinates Using Gold Catalysts 1 liter of an aqueous solution containing 15% by weight of coconut fatty acid monoethanolamide and 15% by weight of potassium cocoylglycinate is placed in a 2 liter pressure autoclave provided with sparging stirrer. This mixture is clear and liquid to 80° C. The amount of potassium cocoylglycinate can be taken from a previous batch or remain in the reactor from a previous oxidation batch. After addition of 5 g of a nanogold catalyst (0.9% by weight of gold and 0.1% by weight of platinum on titanium dioxide, particle size: 4-8 nm), the suspension is brought to a pH of 12 by means of sodium hydroxide and heated to 80° C. After the reaction temperature has been reached, the reaction solution is pressurized with oxygen to a pressure of 9 bar and maintained at this pressure by introduction of further amounts. The pH of the mixture is maintained at 12 over the entire reaction time by means of potassium hydroxide introduced by means of an automatic titrator. After 6 hours, the reactor is cooled, vented and the catalyst is separated off from the reaction solution by filtration. The solution has a residual content of <1% by weight of coconut monoethanolamide and about 33% by weight of potassium cocoylglycinate.

The invention claimed is:

1. A process for preparing at least one acylglycinate salt of the formula (II)

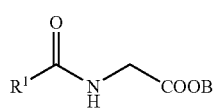

(II)

where
$R^1$ is a saturated linear or branched alkyl radical having from 1 to 21 carbon atoms or a monounsaturated or polyunsaturated linear or branched alkenyl radical having from 2 to 21 carbon atoms and
B is a cation,
and/or the corresponding protonated acylglycine acid, wherein the process comprises the step of oxidizing at least one fatty acid monoethanolamide of the formula (I)

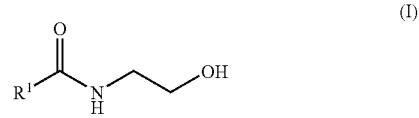

(I)

where $R^1$ is as defined above,
with oxygen in the presence of an optionally supported bimetal catalyst consisting of gold and a metal from group VIII of the Periodic Table of Elements in alkaline medium to form at least one acylglycinate salt of the formula (II) and, in the case of the preparation of the protonated acylglycine acid, additionally reacting the at least one acylglycinate salt of the formula (II) with an acid.

2. A process as claimed in claim 1, wherein $R^1$ is a saturated linear or branched alkyl radical having from 7 to 17 carbon atoms or a monounsaturated or polyunsaturated linear or branched alkenyl radical having from 7 to 17 carbon atoms.

3. A process as claimed in claim 1, wherein the at least one fatty acid monoethanolamide of the formula (I) is selected from the group consisting of lauric acid monoethanolamide, myristic acid monoethanolamide, caprylic acid monoethanolamide, capric acid monoethanolamide, palmitic acid monoethanolamide, stearic acid monoethanolamide, isostearic acid monoethanolamide, coconut fatty acid monoethanolamide and mixtures thereof.

4. A process as claimed in claim 1, wherein the bimetal catalyst has been applied to a support.

5. A process as claimed in claim 4, wherein the bimetal catalyst has been applied to an oxidic support.

6. A process as claimed in claim 5, wherein the oxidic support comprises titanium dioxide.

7. A process as claimed in claim 4, wherein the supported bimetal catalyst contains from 0.1 to 5% by weight of gold.

8. A process as claimed in claim 4, wherein the supported bimetal catalyst contains from 0.1 to 3% by weight of a metal from group VIII.

9. A process as claimed in claim 1, wherein the particle size of the bimetal catalyst is from 1 to 50 nm.

10. A process as claimed in claim 1, wherein a solution comprising at least one fatty acid monoethanolamide of the formula (I) and at least one acylglycinate of the formula (II) is subjected to the oxidizing step.

11. A process as claimed in claim 4, wherein the supported bimetal catalyst contains from 0.5 to 3% by weight of gold.

12. A process as claimed in claim 4, wherein the supported bimetal catalyst contains from 0.1 to 2% by weight of a metal from group VIII.

13. A process as claimed in claim 4, wherein the supported bimetal catalyst contains from 0.1 to 3% by weight of platinum or palladium.

14. A process as claimed in claim 1, wherein the particle size of the bimetal catalyst is from 2 to 10 nm.

\* \* \* \* \*